United States Patent [19]

Antalné et al.

[11] Patent Number: 5,430,017

[45] Date of Patent: Jul. 4, 1995

[54] ORAL PHARMACEUTICAL COMPOSITION CONTAINING CYCLOSPORIN AND PROCESS FOR PREPARING SAME

[75] Inventors: Kovács Antalné; Kiss Tamasné; Jancsó Sándor; Jusztin Istvánné; Kovács István; Takács Erzsébet, all of Debrecen; Orbán Ernó, Budapest; Tomori Lázlóné, Budapest; Kürthy Mária, Budapest; Balogh Tibor, Budapest; Jaszlits László, Budapest; Moravcsik Imre, Budapest, all of Hungary

[73] Assignee: BIOGAL Gyogyszergvar RT, Debrecen, Hungary

[21] Appl. No.: 915,719

[22] Filed: May 20, 1993

[30] Foreign Application Priority Data

Dec. 27, 1990 [HU] Hungary ............................... 8474/90

[51] Int. Cl.$^6$ ..................... A61K 37/00; A61K 31/74; A61K 38/00
[52] U.S. Cl. ........................................... 514/9; 514/11
[58] Field of Search ........................................ 514/9, 11

[56] References Cited

U.S. PATENT DOCUMENTS

| | | | |
|---|---|---|---|
| 4,649,047 | 3/1987 | Kagwari | 514/11 |
| 4,996,193 | 2/1991 | Hewitt et al. | 514/11 |
| 5,051,402 | 9/1991 | Kurihara et al. | 514/11 |

Primary Examiner—Jill Warden
Assistant Examiner—Lynn Touzeau
Attorney, Agent, or Firm—Keil & Weinkauf

[57] ABSTRACT

The invention relates to a pharmaceutical composition for oral administration containing cyclosporin A and/or cyclosporin G as active ingredient, which possess advantageous absorption characteristics, and to a process for preparing this composition. The composition according to the invention comprises 1 part by mass of one or more cyclosporin(s) dissolved in 4 to 50 parts by volume of propylene glycol, 0 to 25 parts by volume of ethanol and 0.0 to 5 parts by mass of a polyoxyethylene/polyoxypropylene block polymer in homogenized state. Based on examinations carried out at 100° C., the stability of solutions prepared according to the invention does not differ from that of the commercially available Sandimmun oral solution.

8 Claims, 1 Drawing Sheet

5,430,017

ORAL PHARMACEUTICAL COMPOSITION CONTAINING CYCLOSPORIN AND PROCESS FOR PREPARING SAME

FIELD OF THE INVENTION

This invention relates to therapeutically useable novel cyclosporin-containing solutions possessing advantageous absorption characteristics and suitable for oral administration. Furthermore, the invention relates to a process for preparing these solutions.

BACKGROUND OF THE INVENTION

Cyclosporins are cyclic oligopeptides of microbiological origin. Due to its immunosuppressive effect, cyclosporin is widely used: in kidney, liver, heart, lung, pancreas, skin and cornea transplatations in order to prevent the ejection of the transplanted organ; in bone marrow transplantations, to inhibit the antibody production of the transplanted bone marrow against the host organism (graft-versus-host disease); further for healing autoimmune diseases such as rheumatoid arthritis, diabetes mellitus I, systematic lupus erythematosis, scleroderma, Wegener's granulomatosis, eosinophilic fascitis, primary liver cyrrhosis, Graves' and Crohn's diseases. Similarly, it is used for the treatment of myasthenia gravis, multiplex sclerosis and psoriasis.

Cyclosporins are practically water-insoluble substances formed from neutral amino acids of hydrophobic character. As a consequence of their high molecular weight (over 1000), poor water-solubility and weak absorption [O. Siddiqui and Y. W. Chien: Nonparenteral Administration of Peptide and Protein Drugs. CRC Crit. Rev. Ther. Drug Car. 3, 195–208 (1986)], they are absorbed only to an insignificant extent from the gastrointestinal tract when administered directly or in the traditional pharmaceutical formulations (tablets, capsules and the like).

Thus, the most important aim of developing cyclosporin-containing pharmaceutical compositions is to find a solution for this problem, by means of which the absorption and bioavailability of the active agent can successfully be improved.

A number of methods are known from the literature, by the use of which the absorption and bioavailability of cyclosporin active agents can be increased. From these, the methods worked out for preparing solutions for oral administration are briefly summarized hereinafter.

1. Dissolution of cyclosporin in sesame oil and/or in the mixture of non-ionic surfactants and/or transesterified nonionic triglycerids and/or lecithins, ethyl oleate and transesterified nonionic surfactants and/or in a neutral oil (see e.g. the Swiss patent specification No. 636,013).

2. Dissolution of cyclosporin in the mixture of a transesterified product of a native vegetable oil with a polyalkylene polyol (such as Labrafil M 1944 CS) as well as a vegetable oil and ethanol (see e.g. the Swiss patent specification No. 641,356 and the U.S. Pat. No. 4,388,307).

The above method 1 is suitable for preparing a drink solution or drink emulsion whereas method 2 is useful for the preparation of a water-dispersible oral solution. It should be noted that the commercially available oral Sandimmun ® solution (Sandoz Ltd., Basel, Switzerland) is prepared according to method 2.

Compositions with relatively high active-ingredient content can be prepared by using both methods. The disadvantage of these compositions lies in that vegetable oils are used as carrier additives which, on the one hand, endow the compositions with an unpleasant oily taste and, on the other hand, these compositions become rancid during a longer storage whereby a further undesired alteration may occur in the taste and odour of the compositions. Although the degree of rancidification could be limited by antioxidants, this process cannot completely be eliminated. Thus, the oral compositions prepared according to the above methods can be commercialized with only a relatively short expiration time.

SUMMARY OF THE INVENTION

The aim of the present invention is to provide therapeutically useful, oral cyclosporin-containing solutions which are free from the drawbacks of the known solutions, contain the cyclosporin active ingredient(s)—in opposition to the known solutions—dissolved in a both chemically and microbiologically stable hydrophilic and not hydrophobic medium and provide advantageous absorption of the active ingredient(s) from the gastrointestinal tract after dilution with water or aqueous solutions.

DETAILED DESCRIPTION OF THE INVENTION

During our investigations it has surprisingly been observed that the above aim could completely be achieved by using suitable hydrophilic pharmaceutical additives (solvents and surface-active agents). It has been stated that the dissolution of one or more cyclosporin(s) in the mixture of propylene glycol and a polyoxyethylene/polyoxypropylene block polymer, optionally in the presence of ethanol, results in solutions from which, after mixing with water or aqueous solutions (e.g. fruit juices, milk, chocolate-drinks), the cyclosporins precipitate in the form of finely distributed, dispersed particles. The cyclosporins are rapidly absorbed from the gastrointestinal tract due to the large surface of particles of the active ingredient as well as under the effect of the block polymer.

The above recognition is also therefore surprising since it is known that the gastrointestinal absorption of drugs of hydrophobic character like the cyclosporins (e.g. griseofulvin, chlorothiazide, nitrofurantoin, indoxol and the like) proceeds with a substantially better efficiency from oily solutions or oil-in-water emulsions than from the corresponding aqueous suspensions of fine distribution. In opposition to the use in empty stomach, the blood levels of these drugs are strongly enhanced by consuming fat-rich foods (e.g. butter, cream) before the administration [M. Gibaldi: Biopharmaceutics and Clinical Pharmaceutics, Lea and Febiger, Philadelphia (1984)].

It is supported by the above-mentioned facts that the absorption of substances of hydrophobic character can preferably be improved by preparing and using lipid-type matrices or solutions. At the same time it is surprising that the absorption of cyclosporins from hydrophilic systems to the same extent as above can be ensured while eliminating lipid-like substances.

The animal experiments carried out for proving our above statements are discussed hereinafter.

Solution to be tested: a solution containing cyclosporin A, prepared according to Example 2, in a concentration of 100 mg/ml.

Test method: 6 male New Zealand rabbits with 2.7 to 3.5 kg of body weight were used in the animal tests. The animals were kept separately at 20°±2° C. and received standard rabbit food (LATI, Gödöllő) as well as tap water ad libitum. (No food was given starting from the afternoon of the day before administration.) The solution to be tested was administered in a dose of 25 ml/kg of body weight through a probe and washed in by the same volume of tap water.

Five ml of blood each were taken from the ear vein of the rabbits before administration and then 1, 2, 3, 4, 6, 12 and 24 hours after administration.

BRIEF DESCRIPTION OF THE DRAWING

The concentration of cyclosporin A in the blood samples was determined by HPLC method. The results obtained are shown in FIG. 1 wherein blood-level values are plotted against time elapsed after oral administration.

It can be stated from the data that cyclosporin A was well adsorbed from the orally administered solution. The highest blood level developed 2 hours following administration. Only an extremely low amount of cyclosporin could be detected in the blood after 24 hours.

Figure 1:
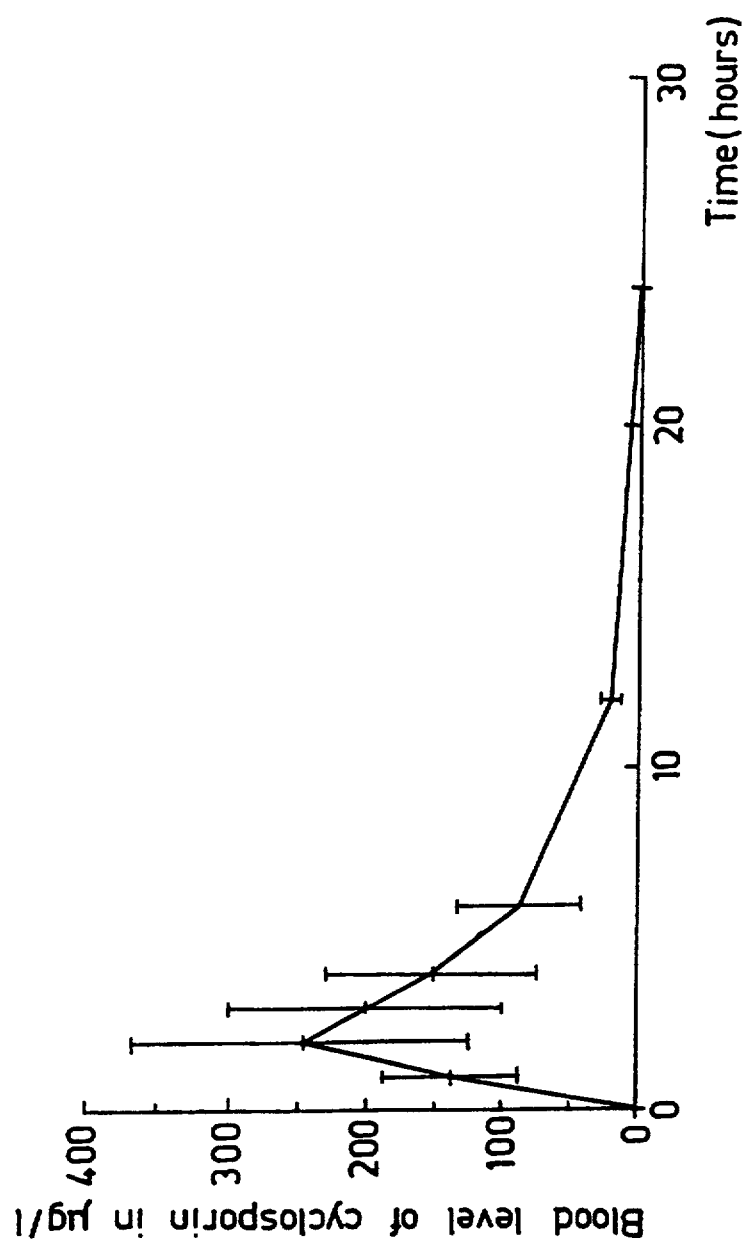

Based on the above results, the invention relates to a novel, therapeutically usable oral solution containing cyclosporin as active ingredient in admixture with hydrophilic solvents and surface-active agents, which comprises 1 part by mass of one or more cyclosporin(s) dissolved in 4 to 50 parts by volume of propylene glycol, 0 to 25 parts by volume of ethanol and 0.01 to 5 parts by mass of a polyoxyethylene/polyoxypropylene block polymer in homogenized and, if desired, sterile state.

According to an other aspect of the invention, there is provided a process for the preparation of the above novel oral solution, which comprises dissolving 1 part by mass of one or more cyclosporin(s) in 4 to 50 parts by volume of propylene glycol, 0 to 25 parts by volume of ethanol and 0.01 to 5 parts by mass of a polyoxyethylene/polyoxypropylene block polymer, homogenizing the solution obtained and, if desired, sterilizing it by filtration.

By using the process according to the invention, hydrophobic cyclopropins, which are insoluble or weakly soluble in the common pharmaceutical additives, e.g. cyclosporin A and cyclosporin G, or any of their mixtures of desired ratio can be brought into a solution being hydrophilic in character and subsequently a dispersion with extremely fine particle size can be prepared from this solution.

Synthetic polyoxyethylene/polyoxypropylene block polymers [nomenclature according to CTFA (Cosmetic, Toiletry and Fragrance Association): Poloxamers] with a molcular mass between 1000 and 15,500, preferably Poloxamer-124, -184, -185, -188, -237, -335, -338 and -407 or their mixtures may be used as surface-active agents in the compositions according to the invention. These block polymers are commercially available under the trade name Pluronic or Lutrol, respectively (manufacturer: BASF Wyandotte Corp. Mich., USA or BASF, Ludwigshafen, Germany). A great advantage of polyoxyethylene/polyoxypropylene block polymers lies in that they are tasteless, extremely stable and possess significant bactericidal or bacteriostatic effects; therefore, no other additives are needed for the microbiological preservation of solutions prepared by using these block polymers [Pluronic Polyols Toxicity and Irritation Data, 3rd Edition, BASF Wyandotte Corp. Wyandotte, Mich., USA (1971)].

The ratio of propylene glycol, ethanol and surface-active agents which can be be used in the cyclosporin-containing oral solutions according to the invention is determined in each case by the cyclosporin concentration of the composition to be prepared.

Thus, propylene glycol is preferably used in a volume ratio of (4 to 50):1; ethanol is preferably used in a volume ratio of (0 to 25):1 and the polyoxyethylene/polyoxypropylene block polymer is preferably employed in a weight ratio of (0.01 to 5):1 in relation to the mass of the cyclosporin(s) used.

According to a preferred embodiment of the process of the invention cyclosporin-containing oral solutions are prepared by dissolving 1 part by mass of cyclosporin and 0.01 to 5 parts by mass of polyoxyethylene/polyoxypropylene block polymer in a mixture containing 4 to 50 parts by volume of propylene glycol and 0 to 25 parts by volume of ethanol (or in 4 to 50 parts by volume of propylene glycol when no ethanol is used) at room temperature (about 20 ° C.).

If desired, the solution obtained is filtered through a regenerated cellulose membrane (Sartorius SM 116 04 with a pore size of 0.8 μm) and filled into suitable glass bottles in the doses required.

The pharmaceutical composition prepared as described above can be administered after dilution with water or aqueous solutions. A suitably dosed (weighed) part of the solution is poured into 100-150 ml of water, fruit juice or cold cocoa drink, mixed and then orally administered.

Thus, by using the process according to the invention, well-absorbable oral cyclosporin compositions can be prepared in a simple way by using additives commonly used in the therapeutical practice. The compositions thus prepared are in themselves tasteless, stable and do not require particular storage conditions and can be stored for an unlimited period.

The invention is illustrated in detail by the following non-limiting Examples.

EXAMPLE 1

Preparation of an oral solution containing cyclosporin A

After dissolving 100 g of cyclosporin A in 490 ml of propylene glycol (USP XXII quality) under stirring at room temperature (about 20° C.) 5 g of a polyoxyethylene/polyoxypropylene block polymer of a molecular mass of about 2200 [CTFA-name: Poloxamer-124) USNF XVII Suppl. I quality] are mixed to the above solution. After supplementing the volume to 500 ml by adding propylene glycol, the solution is filtered through a regenerated cellulose membrane (Sartorius SM 116 04) under nitrogen gas pressure. The composition thus obtained is filled into glass bottles suitable for storage.

The thus-pepared composition contains 200 mg/ml of cyclosporin A.

EXAMPLE 2

Preparation of an oral solution containing cyclosporin A 10 g of polyoxyethylene/polyoxypropylene block polymer (with a molecular mass of about 8400 (CTFA-name: Poloxamer-188) USNF XVII Suppl. I quality) are added to a solution prepared by dissolving 100 g of cyclosporin A in 300 ml of ethanol (USP XXII quality)

while stirring at room temperature (about 20° C.). The solution is stirred under identical conditions until the additive is dissolved, then it is filled up to a volume of 1000 ml with propylene glycol (USP XXII quality). The solution is homogenized by stirring, then filtered through a Sartorius SM 116 04 membrane filter under nitrogen gas pressure and the composition is filled into glass bottles suitable for storage.

The composition prepared in this way contains 100 mg/ml of cyclosporin A.

EXAMPLE 3

Preparation of an oral solution containing cyclosporin G 100 g of cyclosporin G are dissolved in a mixture containing 500 ml of ethanol (USP XXII quality), 2900 ml of propylene glycol (USP XXII quality) and 400 ml (400 g) of polyoxyethylene/polyoxypropylene block polymer with a molecular mass of about 2900 (CTFA name: Poloxamer-184) under stirring at room temperature (about 20° C.), then the solution is filled up to a volume of 4000 ml with propylene glycol.

The mixture is homogenized, then the process described in Example 2 is followed.

The composition prepared in this way contains 25 mg/ml of cyclosporin G.

EXAMPLE 4

Preparation of an oral solution containing cyclosporin A and cyclosporin G 50 g of cyclosporin A and 50 g of cyclosporin G are dissolved in a mixture containing 300 ml of ethanol (USP XXII quality) and 100 ml of propylene glycol (USP XXII quality) while stirring at room temperature (about 20° C.). After adding 10 g of a polyoxyethylene/polyoxypropylene block polymer with a molecular mass of about 7700 (CTFA-name: Poloxamer-237) and 5 g of a polyoxyethylene/polyoxypropylene block polymer with a molecular mass of about 6500 (CTFA-name: Poloxamer-335) the solution is stirred until dissolution of the additives. The mixture is filled up to a volume of 1000 ml with propylene glycol, homogenized and then the procedure described in Example 2 is followed.

The composition prepared as descirbed above contains 50 mg/ml of cyclosporin A and 50 mg/ml of cyclosporin G.

The composition described in Examples 1 to 4 were subjected to stability examinations. The solutions were stored at 25°, 45°, 60°, 75 ° and 100° C., respectively, after filling into brown glass bottles of III hydrolytic class.

Simultaneously with the examination of solutions prepared according to the process of the invention, the stability of the commercially available Sandimmun ® drink solution (Sandoz Ltd, Basel, Switzerland) containing 100 mg/ml of cyclosporin A was also examined.

The quantitative determination of cyclosporin A was performed by using HPLC method under the following conditions of chromatography:

Pump: LKB Model 2150
Controller: LKB 2152
Detector: LKB Model 2151 with a variable wavelength UV absorbance at 220 nm, 0.64 AB
LKB Model 2140 serieal diode detector
Injector: Rheodyne, Model 7215, 10 μl of loop injection
Column: BST-Si-100 C 8.7 μm, 25 cm×0.4 cm stainless steel
Thermostat: LK Model 2155, maintaining the column at 50° C. during the analysis
Eluant: acetonitrile/water/methanol/85 % phosphoric acid (900:525:75:0.075)
Flow rate of the eluant: 1 ml/min
Integrator: LKB Model 2220
Recorder: LKB Model 2210, 10 mV It has been stated by the above examinations that the stability of solutions prepared according to the process of the invention did not differ from the stability of the commercially available composition. This statement is illustrated in Table I by the results of examinations carried out at 100° C. with a solution containing 100 mg/ml of cyclosporin A (signed as CyA in Table I) prepared in Example 2 according to the invention and, on the other hand, with a Sandimmun ® drink solution of the same concentration.

TABLE I

Comparative stability examination of oral solutions containing cyclosporin A

| Thermal load | Oral solution of Ex. 2. CyA content (measured in %) | n (%) | Sandimmun oral solution CyA content (measured in %) | n(%) |
|---|---|---|---|---|
| Untreated | 96.1 ($n_1$) | 98.9 | 99.3 | 99.8 |
|  | 96.6 ($n_2$) |  | 100.6 |  |
|  | 96.9 ($n_3$) |  | 99.5 |  |
| 100°/1 hour | 97.6 | 98.9 | 100.6 | 100.0 |
|  | 99.7 |  | 99.3 |  |
|  | 99.4 |  | 100.2 |  |
| 100°/5 hours | 96.4 | 95.3 | 97.5 | 97.3 |
|  | 95.4 |  | 96.6 |  |
|  | 94.1 |  | 97.8 |  |
| 100°/8 hours | 98.0 | 96.7 | 98.5 | 98.1 |
|  | 95.2 |  | 97.6 |  |
|  | 97.1 |  | 98.0 |  |
| 100°/24 hours | 97.8 | 96.6 | 96.0 | 95.5 |
|  | 98.7 |  | 95.8 |  |
|  | 93.3 |  | 94.9 |  |

We claim:

1. A pharmaceutical composition for oral administration, which comprises as active ingredient 1 part by mass of cyclosporin A or cyclosporin G, or a mixture thereof, dissolved in 4 to 50 parts by volume of propylene glycol, 0 to 25 parts by volume of ethanol and 0.01 to 5 parts by mass of a polyoxyethylene/polyoxypropylene block polymer.

2. The composition of claim 1 wherein the block polymer is in an homogenized and sterile state.

3. A composition as claimed in claim 1, which comprises cyclosporin A or cyclosporin G or a mixture thereof as cyclosporin.

4. A composition as claimed in claim 1, which comprises using a polyoxyethylene/polyoxypropylene block polymer with a molecular mass between 1000 to 15,500.

5. A process for the preparation of the pharmaceutical composition of claim 1, which comprises dissolving 1 part by mass of one or more cyclosporin(s) in a mixture containing 4 to 50 parts by volume of propylene glycol, 0 to 25 parts by volume of ethanol and 0.01 to 5 parts by mass of a polyoxyethylene/polyoxypropylene block polymer, homogenizing the solution obtained.

6. The process of claim 5 wherein the solution is sterilized by filtration.

7. A process as claimed in claim 5, which comprises using cyclosporin A or cyclosporin G or a mixture thereof as cyclosporin.

8. A process as claimed in claim 5, which comprises using a polyoxyethylene/polyoxypropylene block polymer with a molecular weight between 1000 and 15,500.

* * * * *

UNITED STATES PATENT AND TRADEMARK OFFICE
CERTIFICATE OF CORRECTION

PATENT NO.: 5,430,017

DATED: July 4, 1995

INVENTOR(S): ORBAN et al.

It is certified that error appears in the above-identified patent and that said Letters Patent is hereby corrected as shown below:

On the cover page, item [75], the name, "Lázlóné" should be --Lászlóné--.

On the cover page, item [30], delete the presently listed priority information and substitute --Nov. 27, 1990 [HU] Hungary ..... 7653/90--.

In the Abstract, line 9, "0.0" should read --0.01--.

Signed and Sealed this

Seventh Day of November, 1995

Attest:

BRUCE LEHMAN

*Attesting Officer*  *Commissioner of Patents and Trademarks*